United States Patent [19]
Kuo et al.

[11] Patent Number: 5,569,770
[45] Date of Patent: Oct. 29, 1996

[54] METHOD FOR THE PRODUCTION OF N-VINYL-2-PYRROLIDONE BY GAS-PHASE DEHYDRATION REACTION AT ATOMOSPHERIC PRESSURE

[75] Inventors: Pine-Sci Kuo, Hsinchu Hsien; Shiao-Jung Chu, Hsinchu; Chu-Chang Dai, Hsinchu Hsien; Hsi-Yen Hsu, Taipei; Ching-Tang Lin; Yi-Yun Lin, both of Hsinchu, all of Taiwan

[73] Assignee: Industrial Technology Research Institute, Chutung Hsinchu, Taiwan

[21] Appl. No.: 594,549

[22] Filed: Jan. 31, 1996

[51] Int. Cl.$^6$ .................................................. C07D 207/267
[52] U.S. Cl. .................... 548/543; 548/552; 502/201; 502/226; 502/227; 502/262; 502/308; 502/309; 502/310
[58] Field of Search ...................................... 548/552, 543

[56] References Cited

U.S. PATENT DOCUMENTS

| | | | |
|---|---|---|---|
| 2,669,570 | 2/1954 | Schnizer et al. | 548/543 |
| 2,775,599 | 12/1956 | Puetzer et al. | 548/543 |
| 3,821,245 | 6/1974 | Kanetaka et al. | 548/543 |

Primary Examiner—David B. Springer
Attorney, Agent, or Firm—W. Wayne Liauh

[57] ABSTRACT

The present invention relates to a method for the production of N-vinyl-2-pyrrolidone by gas-phase reaction at atmospheric pressure. The method is characterized in that a gas-phase reaction is conducted by using N-β-Hydroxyethyl-2-Pyrrolidones serving as raw materials, at a temperature of 300°–450° C., a space velocity of 500–4500 hr$^{-1}$ in the presence of a mixed oxide of group IV elements, or an oxide of group IV elements, which has been modified by group I or group II elements.

25 Claims, No Drawings

METHOD FOR THE PRODUCTION OF N-VINYL-2-PYRROLIDONE BY GAS-PHASE DEHYDRATION REACTION AT ATMOSPHERIC PRESSURE

BACKGROUND OF THE INVENTION

1. Field of the Invention

The present invention relates to a method for the production of N-vinyl-2-pyrrolidone by gas-phase dehydration reaction at atmospheric pressure, in particular to a method for producing N-vinyl-2-pyrrolidone by dehydrating N-(β-hydroxyethyl)-2-pyrrolidone employing a mixed oxide of group IV elements as catalyst at a temperature of 300°–450° C. and at a space velocity of 500–4500 $hr^{-1}$.

2. Description of the Prior Art

N-vinyl-2-pyrrolidone is a valuable and useful fine chemical. Due to its unique physical properties such as water solubility, high polarity, nontoxicity, chemical stability and cation activity, it has been widely applied in the manufacture of adhesives, paints, textiles, foods and personal medicines. The homopolymers or copolymers thereof have improved film strength, dye compatibility, rigidity and adhesion.

Conventionally, N-vinyl-2-pyrrolidone is produced by utilizing the "Reppe Reaction" to subject 2-pyrrolidone and acetylene to vinylation. However, there are various difficulties with the acetylene employing Reppe Reaction. Moreover, acetylene is easy to explode, and is thus difficult to transport and handle. Consequently, alternative methods have been proposed. Among them, process employing N-(β-hydroxyethyl)-2-pyrrolidone as raw materials is deemed as most desirable process. For example, in U.S. Pat. No. 2,775,599 issued to Puetzer et al, it is disclosed that N-vinyl-2-pyrrolidone is obtained by reacting N-(β-hydroxyethyl)-2-pyrrolidone with thionyl chloride to form N-β-chloroethyl-2-pyrrolidone, followed by removing hydrogen chloride. Also, U.S.S.R. Patent No. 125,567 discloses a method which involves reacting N-(β-hydroxyethyl)-2-pyrrolidone with acetic anhydride to form ester, followed by removing acetic anhydride to obtain N-vinyl-2-pyrrolidone. Methods for producing N-vinylpyrrolidone by directly dehydrating N-(β-hydroxyethyl)-2-pyrrolidone without the formation of intermediates are disclosed in, for example U.S. Pat. No. 2,669,570. According to the production method of said patent, the dehydration reaction is carried out by directly contacting N-(β-hydroxyethyl)-2-pyrrolidone with dehydration catalysts at a temperature of 300°–340° C., and under sub-atmosphereic pressures below 100 mm of mercury at a hourly vapor space velocity of 500–4000 $hr^{-1}$. The employed dehydration catalysts are active aluminum, calcium oxide-aluminum or iron oxide-potassium hydroxide. By using active aluminum, N-vinyl-2-pyrrolidone is produced by yields above 64 mole %. The catalytic dehydration process, however, should be carried out at a reduced pressure below 100 mm of mercury, and thus is not practical for industrial production.

U.S. Pat. No. 3,821,245 discloses a method for producing N-vinyl-2-pyrrolidone by dehydrating N-(β-hydroxyethyl)-2-pyrrolidone employing an oxide selected from zirconium oxide, thorium oxide, cerium oxide, zinc oxide and chromium oxide as a catalyst. The yield of the method is improved and the reaction can be conducted at atmospheric pressure. Among these oxides, zirconium oxide has the best catalytic activity, and when the reaction is carried out at 350° C. at a space velocity of 1800 $hr^{-1}$ for 2.5 hours, the conversion of N-(β-hydroxyethyl)-2-pyrrolidone can reach 95.7 mole %. However, disadvantages of the method are that the selectivity of N-vinyl-2-pyrrolidone is not high, merely 73.8 mole %, and its catalyst life is short. When the reaction proceeds for 50 hours, the conversion rapidly drops to 80 mole %, and thus the method is not suitable for industrial production.

SUMMARY OF THE INVENTION

It is therefore an object of the present invention to provide a method for the production of N-vinyl-2-pyrrolidone by which method, the yield is improved, the catalyst life is lengthened, and the dehydration reaction can be conducted at atmospheric pressure.

The object of the invention is attained by employing a mixed oxide of group IV elements as catalysts.

Specifically, the method of the invention includes dehydrating N-(β-hydroxyethyl)-2-pyrrolidone in the presence of a mixed oxide of group IV elements at a temperature of 300°–450° C., at a space velocity of 500–4500 $hr^{-1}$. The mixed oxide is a mixture of at lease two oxides of group IV elements, and the oxides are selected from zirconium oxide, tin oxide, titanium oxide, silicon oxide and hafnium oxide. The oxides can be modified with alkali metal or alkaline earth metal oxides.

According to an aspect of the present invention, the dehydration reaction can be carried out at atmospheric pressure and the yield of N-vinyl-2-pyrrolidone can reach 84 mole %. The by-product of the dehydration reaction is valuable 2-pyrrolidones, and thus the total yield can be higher than 95 mole %.

According to another aspect of the present invention, the surface of the mixed oxide catalysts of the present invention contains both active acid and base sites. The acidity and basicity of the acid sites and basic sites are moderate, and thus are especially suitable for the catalytic dehydration of N-(β-hydroxyethyl)-2-pyrrolidone. And as no special strong acid sites exist on the surface of the catalysts, the formation of cracking products can be inhibited, and thus the catalyst life can be lengthened. Moreover, as the surface of the catalysts contains both active acid sites and basic sites, the activity of the catalysts of the present invention is rather high, and thus the selectivity of the product, N-vinyl-2-pyrrolidone exceeds 90 mole %

The present invention can be more fully understood by reading the subsequent detailed description and examples.

DETAILED DESCRIPTION OF THE INVENTION

The mixed oxides according to the present invention are mixed oxides of group IV elements. Examples of suitable oxides include zirconium oxide, tin oxide, titanium oxide, silicon oxide and halfnium oxide. The mixed oxides can be a mixture of two or at least two of the above oxides. Preferred combinations are zirconium oxide-tin oxide, zirconium oxide-titanium oxide, zirconium oxide-silicon oxide, or zirconium oxide-hafnium oxide. The content of zirconium in the above combinations is preferably 10–99 wt %, and more preferably 50–99 wt %.

The above mixed oxides can be prepared by coprecipitation. The coprecipitation method includes mixing the salts of group IV elements, such as their chlorides or nitrates, in a suitable solvent such as water or alcohol, adjusting the pH value of the resulting solution to 8–11 to form hydroxide precipitate, and then filtering, washing, drying and calcining the hydroxide precipitate at 300°–1000° C. for 2–12 hours to form the catalyst. The mixed oxides can also be prepared by other methods such as impregnation or kneading methods.

The mixed oxide dehydration catalysts of the present invention can be modified by impregnating them in an aqueous solution containing alkali metal elements or alkaline earth metal elements for several hours, followed by drying and calcining at 300°–1000° C. for several hours. The amount of the alkali metal elements or alkaline earth metal elements contained in the modified catalysts should be not more than 1.0 wt %.

The dehydration catalysts of the present invention can be easily regenerated. For example, introducing air or oxygen-containing gases or steam and treating at 400°–700° C. for 2–5 hours can recover the activity of the catalysts.

The catalytic dehydration reaction is preferably carried out at 250°–500° C., more preferably at 300°–450° C. If the dehydration reaction is carried out at a temperature below 250° C., the conversion is rather low and thus is not practical, and if the reaction is carried out at a temperature above 500° C., the cracking products increase. The dehydration reaction can be carried out at atmospheric pressure, reduced pressure or at a pressure higher than atmospheric pressure. The gaseous space velocity (GHSV) of the feed, according to the present invention, is about 500–4500 $hr^{-1}$, preferably 900–3600 $hr^{-1}$. The N-(β-hydroxyethyl)-2-pyrrolidone can be fed after it is gasified or be fed by a mixed feed method after it is diluted with inert gases such as nitrogen gas.

As aforesaid, the by-product of the catalytic dehydration reaction of the present invention is 2-pyrrolidone which is a valuable substance. The by-product can be easily separated from the product, N-vinyl-2-pyrrolidone, for example, by reduced pressure distillation. Also, according to the method of the invention, the selectivity of N-vinyl-2-pyrrolidone is rather high, usually above 90 mole %.

The examples which follow illustrate the method according to the present invention without implying any limitations. In these examples, the dehydration reaction is carried out in a fixed bed reactor at atmospheric pressure. The fixed bed reactor is a ⅜ inch diameter, 60 cm long stainless tube in which the catalyst bed is 5–10 cm in height. The outside preheating zone is controlled at 300° C., and the reaction temperature is controlled at 300°–400° C. The reactant N-(β-hydroxyethyl)-2-pyrrolidone is pumped to the top of the tube reactor, mixing with nitrogen gas at a 1:1 molar ratio and then introduced into the reactor. The gasous space velocity is maintained at 500–4500 $hr^{-1}$. The products are collected after condensation, and a portion of the collected products is used to quantify the compositions of the products by a HP 5890 gas chromatograph using HP-FFAP (0.53×30 m capillary column) as separation column and FID detector.

Conversion, yield and selectivity are calculated respectively by the following equations (1), (2) and (3).

conversion(mole %) = (1)

$$\frac{\text{(mole of N-β-Hydroxyethyl-2-pyrrolidone)}_{before\ reaction} - \text{(mole of N-β-Hydroxyethyl-2-pyrrolidone)}_{after\ reaction}}{\text{(mole of N-β-Hydroxyethyl-2-pyrrolidone)}_{before\ reaction}} \times 100\%$$

yield of N-vinyl-2-pyrrolidone (mole %) = (2)

$$\frac{\text{(mole of N-vinyl-2-pyrrolidone)}_{after\ reaction}}{\text{(mole of N-β-Hydroxyethyl-2-pyrrolidone)}_{before\ reaction}} \times 100\%$$

selectivity of N-Vinyl-2-pyrrolidone (mole %) = (3)

$$\frac{\text{(mole of N-vinyl-2-pyrrolidone)}_{before\ reaction}}{\text{(mole of N-β-Hydroxyethyl-2-pyrrolidone)}_{before\ reaction} - \text{(mole of N-β-Hydroxyethyl-2-pyrrolidone)}_{after\ reaction}} \times 100\%$$

EXAMPLE 1

214 g of zirconium oxychloride ($ZrOCl_2 \cdot 8H_2O$) and 19 g of titanium chloride ($TiCl_4$) were respectively dissolved in anhydrous ethanol, and the resulting solutions were mixed homogeneously. Ammonia water was dropped into the resulting mixture. The addition of ammonia water was stopped when the pH value of the solution reached 10. A viscous mixture was formed, and the viscous mixture was thereafter filtered, washed, and dried. The dried mixture was then calcined at 550° C. for 4 hours, compressed and grounded into 30–50 mesh.

3 ml of the grounded catalyst was placed in a stainless tube reactor as mentioned above. The preheated zone was maintained at a temperature of 300° C., and the reaction zone was maintained at 370° C. N-(β-Hydroxyethyl)-2-pyrrolidone was supplied to the reaction tube at a rate of 10 g/hr together with nitrogen gas as carrier ( at 30 cc/min), whereby a total space velocity of 3600 $hr^{-1}$ was obtained. Liquid products obtained during a reaction period from 2.0 to 2.5 hours were collected and quantified by Gas Chromatography. As a result, it was found that the conversion of the N-(β-Hydroxyethyl)-2-pyrrolidone was 91.0 mole %, the selectivity of N-vinyl-2-pyrrolidone was 76.3 mole % and the selectivity of 2-pyrrolidone was 21.6 mole %.

EXAMPLE 2

296 g of zirconium oxychloride ($ZrOCl_2 \cdot 8H_2O$) and 26 g of tin chloride ($SnCl_4$) were respectively dissolved in anhydrous ethanol, and the resulting solutions were mixed homogeneously. Ammonia water was dropped into the resulting mixture. The addition of ammonia water was stopped when the pH value of the solution reached 9. A viscous mixture was formed, and the viscous mixture was thereafter filtered, washed, and dried. The dried mixture was then calcined at 500° C. for 4 hours, compressed and grounded into 30–50 mesh.

3 ml of the grounded catalyst was placed in a stainless tube reactor as mentioned above. The preheated zone was maintained at a temperature of 300° C., and the reaction zone was maintained at 360° C. N-(β-Hydroxyethyl)-2-pyrrolidone was supplied to the reaction tube at a rate of 10 g/hr together with nitrogen gas as carrier (at 30 cc/min), whereby a total space velocity of 3600 $hr^{-1}$ was obtained. Liquid products obtained during a reaction period from 2.0 to 2.5 hours were collected and quantified by Gas Chromatography. As a result, it was found that the conversion of the N-(β-Hydroxyethyl)-2-pyrrolidone was 99.2 mole %, the selectivity of N-vinyl-2-pyrrolidone was 88.7 mole % and the selectivity of 2-pyrrolidone was 10.7 mole %.

EXAMPLE 3

A catalyst as prepared as specified in Example 2 was employed, and the reaction was conducted under similar conditions except that the reaction temperature was 330° C. It was found that the conversion of the N-(β-Hydroxyethyl)-2-pyrrolidone was 84.0 mole %, the selectivity of N-vinyl-2-pyrrolidone was 97.1 mole % and the selectivity of 2-pyrrolidone was 2.9 mole %.

COMPARATIVE EXAMPLE 1

214 g of zirconium oxychloride was dissolved in anhydrous ethanol, and ammonia water was dropped into the resulting solution. The addition of ammonia water was stopped when the pH value of the solution reached 10. Thereafter, catalyst was prepared and dehydration reaction was conducted as described in Example 3. It was found that the conversion of the N-(β-Hydroxyethyl)-2-pyrrolidone was 42.1 mole %, the selectivity of N-vinyl-2-pyrrolidone was 89.1 mole % and the selectivity of 2-pyrrolidone was 4.2 mole %.

EXAMPLE 4

In this example, a catalyst was prepared as described in Example 2 but calcined at 900° C., and the dehydration reaction was conducted under similar conditions except that the reaction temperature was 370° C. It was found that the conversion of the N-(β-Hydroxyethyl)-2-pyrrolidone was 83.4 mole %, the selectivity of N-vinyl-2-pyrrolidone was 94.0 mole % and the selectivity of 2-pyrrolidone was 6.0 mole %.

COMPARATIVE EXAMPLE 2

In this comparative example, a catalyst prepared as described in comparative Example 1 was employed, and the reaction was conducted under similar conditions except that the reaction temperature was 370° C. It was found that the conversion of the N-(β-Hydroxyethyl)-2-pyrrolidone was 99.5 mole %, the selectivity of N-vinyl-2-pyrrolidone was 65.9 mole % and the selectivity of 2-pyrrolidone was 32.9 mole %.

EXAMPLE 5

50 g of Sn—Zr catalyst, which was prepared by a method similar to that set forth in Example 2, was then modified by being impregnation in a 200 ml, 0.001 g potassium hydroxide containing aqueous solution, and then calcined. Dehydration reaction was then conducted under similar conditions by using the obtained catalyst. The conversion of N-(β-Hydroxyethyl)-2-pyrrolidone (NHEP) and the selectivity of N-vinyl-2-pyrrolidone (NVP) are summarized in Table 1.

EXAMPLE 6

In this example, a Sn—Zr catalyst was prepared as described in Example 5 but a 200 ml, 0.5 g calcium hydroxide containing aqueous solution was used to modify the catalyst. The same reaction conditions as in Example 5 were used. The results thus obtained are summarized in Table 1.

EXAMPLE 7

In this example, a catalyst was prepared as described in Example 1 but ethylene glycol was used as solvent, and the calcination temperature was 600° C. The dehydration reaction was also conducted under similar conditions except that the reaction temperature was 350° C. It was found that the conversion of the N-(β-Hydroxyethyl)-2-pyrrolidone was 93.9 mole %, the selectivity of N-vinyl-2-pyrrolidone was 88.7 mole %.

EXAMPLE 8

In this example, a catalyst was prepared as described in Example 2 and the dehydration reaction was conducted under similar conditions except that the reaction temperature was 330° C. and the total space velocity was 900hr$^{-1}$. It was found that the conversion of the N-(β-Hydroxyethyl)-2-pyrrolidone was 96.3 mole %, the selectivity of N-vinyl-2-pyrrolidone was 87.2 mole %.

COMPARATIVE EXAMPLE 3

In this comparative Example 3, the same catalyst as Comparative Example 1 and the reaction conditions as set forth in Example 8 were used. It was found that the conversion of the N-(β-Hydroxyethyl)-2-pyrrolidone was 52.4 mole %, the selectivity of N-vinyl-2-pyrrolidone was 84.1 mole %.

EXAMPLE 9

In this example, the same catalyst composition as Example 2 was used, but water was used as solvent, and the calcination temperate was 500° C. and the reaction temperature was 350° C. It was found that the conversion of the N-(β-Hydroxyethyl)-2-pyrrolidone was 94.4 mole %, the selectivity of N-vinyl-2-pyrrolidone was 90.9 mole %.

EXAMPLE 10

In this example, the same catalyst preparation method and reaction as Comparative Example 2 were used except that 50 g of the resulting $ZrO_2$ catalyst was first impregnated in a 200 ml, 0.001 g potassium hydroxide containing aqueous solution for modification and then subjected to calcin before it was used for dehydration reaction. The results are summarized in Table 2.

EXAMPLE 11

The same catalyst preparation method and reaction as Example 10 were used except that the catalyst was impregnated in a 200 ml, 0.5 g calcium hydroxide containing aqueous solution before it was used for dehydration reaction. The results are also summarized in Table 2.

TABLE 1

| Example No. | promoters | catalyst calcination temperature (°C.) | reaction temperature (°C.) | conversion (%) | NVP selectivity (%) |
| --- | --- | --- | --- | --- | --- |
| 5 | potassium hydroxide | 800 | 360 | 96.8 | 92.1 |
| 6 | calcium hydroxide | 500 | 360 | 96.4 | 94.3 |

TABLE 2

| Example No. | promoters | catalyst calcination temperature (°C.) | reaction temperature (°C.) | conversion (%) | NVP selectivity (%) |
|---|---|---|---|---|---|
| 10 | potassium hydroxide | 800 | 370 | 98.9 | 81.8 |
| 11 | calcium hydroxide | 500 | 370 | 97.8 | 85.8 |

EXAMPLE 11

Catalyst produced in a manner similar to that in Example 2 was employed and the dehydration reaction of N-(β-Hydroxyethyl)-2-pyrrolidone was continued for 100 hours under similar conditions to test the catalyst life. The results thus obtained are summarized in Table 3. It is seen from Table 3 that the yield is very high, the catalyst life is long and the conversion of N-(β-Hydroxyethyl)-2-pyrrolidone is still higher than 80 mole % even the reaction has proceeded for 100 hours.

TABLE 3

| | time from start of reaction (hr) | | | | | | |
|---|---|---|---|---|---|---|---|
| | 10 | 20 | 30 | 40 | 50 | 70 | 100 |
| NHEP conversion (mole %) | 99.6 | 96.8 | 97.2 | 92.3 | 91.8 | 83.2 | 82.8 |
| NVP selectivity (mole %) | 78.9 | 91.3 | 90.2 | 94.6 | 94.6 | 97.1 | 97.2 |
| 2-P selectivity (mole %) | 20.0 | 8.2 | 8.7 | 4.9 | 4.7 | 2.9 | 2.8 |

What is claimed is:

1. A method for the production of N-vinyl-2-pyrrolidone, comprising the following steps:
   (a) subjecting N-(β-Hydroxyethyl)-2-pyrrolidones to dehydration in gaseous phase, at atmospheric pressure, at a temperature of 300°–450° C., at a space velocity of 500–4500 $hr^{-1}$ in the presence of a mixed oxide of group IV elements, to form N-vinyl-2-pyrrolidone and 2-pyrrolidone; and
   (b) separating said N-vinyl-2-pyrrolidone.

2. The method as claimed in claim 1, wherein the mixed oxide of group IV elements is a mixture of at least two oxides, each oxide is selected from zirconium oxide, tin oxide, titanium oxide, silicon oxide, and hafnium oxide.

3. The method as claimed in claim 2, wherein said mixed oxide of group IV elements is a mixture of zirconium oxide and tin oxide.

4. The method as claimed in claim 2, wherein said mixed oxide of group IV elements is a mixture of zirconium oxide and titanium oxide.

5. The method as claimed in claim 2, wherein said mixed oxide of group IV elements is a mixture of zirconium oxide and silicon oxide.

6. The method as claimed in claim 2, wherein said mixed oxide of group IV elements is a mixture of zirconium oxide and hafnium oxide.

7. The method as claimed in claim 3, wherein the content of the zirconium in the mixture is 10–99 wt %.

8. The method as claimed in claim 7, wherein the content of the zirconium in the mixture is 50–99 wt %.

9. The method as claimed in claim 4, wherein the content of the zirconium in the mixture is 10–99 wt %.

10. The method as claimed in claim 9, wherein the content of the zirconium in the mixture is 50–99 wt %.

11. The method as claimed in claim 5, wherein the content of the zirconium in the mixture is 10–99 wt %.

12. The method as claimed in claim 11, wherein the content of the zirconium in the mixture is 50–99 wt %.

13. The method as claimed in claim 6, wherein the content of the zirconium in the mixture is 10–99 wt %.

14. The method as claimed in claim 13, wherein the content of the zirconium in the mixture is 50–99 wt %.

15. The method as claimed in claim 1, wherein the mixed oxide of group IV elements are further modified with alkali metal elements or alkaline earth elements.

16. The method as claimed in claim 15, wherein the modified mixed element contains not more than 1.0 wt % of alkali metal elements or alkaline earth elements.

17. The method as claimed in claim 16, wherein the alkali metal elements are selected from Na, K and Cs.

18. The method as claimed in claim 16, wherein the alkaline earth elements are selected from Mg, Ca and Sr.

19. A method for the preparation of mixed oxide of group IV elements IV serving as catalysts for the production of N-vinyl-2-pyrrolidone, comprising the following steps:
   (a) mixing salts of group IV elements in a suitable solvent;
   (b) adjusting the pH value of the resulting solution to 8–11 to form hydroxide precipitate;
   (c) calcining the hydroxide precipitate at 300°–1000° C. for 2–12 hours to obtain the mixed oxide.

20. The method as claimed in claim 19, wherein the salts of group IV elements are chlorides.

21. The method as claimed in claim 19, wherein the salts of group IV elements are nitrates.

22. The method as claimed in claim 19, wherein in step (b) the PH value is adjusted by adding ammonium water or urea to the resulting solution.

23. The method as claimed in claim 19, wherein in step (a) the solvent is selected from water, alcohol, and ether.

24. The method as claimed in claim 23, wherein the alcohol is ethanol or ethylene glycol.

25. The method as claimed in claim 19, further comprising the following steps:
   (d) modifying the resulting mixed oxide by impregnating an aqueous solution of alkali metals or alkaline earth metals, and drying; and
   (e) calcining the modified mixed oxide at 300°–1000° C.

* * * * *